United States Patent
Momose et al.

(10) Patent No.: US 10,481,110 B2
(45) Date of Patent: Nov. 19, 2019

(54) RADIOGRAPHIC IMAGE GENERATING DEVICE

(71) Applicants: Tohoku University, Sendai-shi Miyagi (JP); Rigaku Corporation, Akishima-shi (JP)

(72) Inventors: Atsushi Momose, Sendai (JP); Takafumi Koike, Akishima (JP); Masahiro Nonoguchi, Akishima (JP)

(73) Assignees: Tohoku University, Sendai-shi (JP); Rigaku Corporation, Akishima-shi (JP)

( * ) Notice: Subject to any disclaimer, the term of this patent is extended or adjusted under 35 U.S.C. 154(b) by 95 days.

(21) Appl. No.: 15/755,923

(22) PCT Filed: Aug. 19, 2016

(86) PCT No.: PCT/JP2016/074209
§ 371 (c)(1),
(2) Date: Feb. 27, 2018

(87) PCT Pub. No.: WO2017/033854
PCT Pub. Date: Mar. 2, 2017

(65) Prior Publication Data
US 2018/0356355 A1    Dec. 13, 2018

(30) Foreign Application Priority Data
Aug. 27, 2015 (JP) .................. 2015-167856

(51) Int. Cl.
*G01N 23/20* (2018.01)
*A61B 6/00* (2006.01)
*G06K 9/46* (2006.01)

(52) U.S. Cl.
CPC ......... *G01N 23/20075* (2013.01); *A61B 6/00* (2013.01); *A61B 6/4035* (2013.01);
(Continued)

(58) Field of Classification Search
None
See application file for complete search history.

(56) References Cited

U.S. PATENT DOCUMENTS

| | | |
|---|---|---|
| 5,812,629 A | 9/1998 | Clauser |
| 2012/0281811 A1* | 11/2012 | Kohara .................... A61B 6/06 378/62 |

(Continued)

FOREIGN PATENT DOCUMENTS

| | | |
|---|---|---|
| JP | 2008-145111 A | 6/2008 |
| JP | 2009-240378 A | 10/2009 |

(Continued)

OTHER PUBLICATIONS

Takeda et al., "Fourier-transform method of fringe-pattern analysis for computer-based topography and interferometry," *J. Opt. Soc. Am.* 72(1):156-160, 1982.

Momose et al., "High-speed X-ray phase imaging and X-ray phase tomography with Talbot interferometer and white synchrotron radiation," *Optics Express* 17(15):12540-12545, 2009.

*Primary Examiner* — Hoon K Song
(74) *Attorney, Agent, or Firm* — Seed Intellectual Property Law Group LLP

(57) ABSTRACT

A device that uses a grating to carry out high sensitivity radiographic image shooting using the wave nature of x-rays or the like can shoot a sample that moves relative to a device. A pixel value computation section determines, using a plurality of intensity distribution images of a sample that moves in a direction that traverses the path of radiation, whether or not a point (p, q) on the sample belongs in a region (Ak) on each intensity distribution image. Further, the pixel value computation section obtains a sum pixel value (Jk) for each region (Ak) by summing pixel values on the each intensity distribution image for point (p, q) that belongs (Continued)

to each region (Ak). An image computation section creates a required radiographic image using the sum pixel values (Jk) of the region (Ak).

12 Claims, 12 Drawing Sheets

(52) U.S. Cl.
CPC ........... *A61B 6/4291* (2013.01); *G01N 23/20* (2013.01); *G01N 2223/309* (2013.01); *G01N 2223/41* (2013.01); *G06K 9/4647* (2013.01)

(56) References Cited

U.S. PATENT DOCUMENTS

| | | | |
|---|---|---|---|
| 2015/0092914 A1* | 4/2015 | Anton | G01N 23/20075 378/36 |
| 2016/0252470 A1* | 9/2016 | Momose | G01N 23/20075 378/36 |

FOREIGN PATENT DOCUMENTS

| | | |
|---|---|---|
| JP | 2009-543080 A | 12/2009 |
| JP | 2012-16370 A | 1/2012 |
| JP | 2013-513413 A | 4/2013 |
| JP | 2013-513417 A | 4/2013 |
| JP | 2013-529984 A | 7/2013 |
| WO | 2004/058070 A1 | 7/2004 |
| WO | 2015/064723 A1 | 5/2015 |

* cited by examiner (a)    (b)    (c)    (d)    (e)

x ↓

(a)  (b)  (c)  (d)  (e)  (f)  (g)  (h)  (i)

RADIOGRAPHIC IMAGE GENERATING DEVICE

BACKGROUND

Technical Field

The present disclosure relates to technology for observing the internal structure of a sample at high sensitivity, utilizing wave properties of radiation that has passed through a test object, such as X rays.

Description of the Related Art

Radiation of high penetrating power, for example X-rays, are in widespread use as probes for visualizing the inside of a material in fields such as medical image diagnosis, non-destructive testing, security checks, etc. Contrast of an X-ray perspective image depends on difference in X-ray attenuation factor, and a body that strongly absorbs X-rays is rendered as an X-ray shadow. X-ray absorption power is stronger the more elements are contained that have a larger atomic number. Conversely, for a material that is composed of elements of small atomic number, it can be noted that it is also difficult to obtain contrast, and this is also a principle disadvantage with conventional X-ray perspective images. Accordingly, it has not been possible to obtain sufficient sensitivity with regard to soft biological tissue, organic material, etc.

On the other hand, if the wave properties of X-rays are utilized, it is possible to realize a sensitivity increase of up to about three orders of magnitude compared to general conventional X-ray perspective images. Hereafter this will be referred to as an X-ray phase contrast method. If this technology is applied to observation of materials composed of light elements that do not absorb X-rays well (such as soft biological tissue, organic material, etc.), then since examination becomes possible that was difficult with the conventional methods, such practical application is expected.

A method that uses a transmission grating is known as an approach for realizing a high sensitivity imaging method that utilizes the X-ray phase contrast method (refer to patent publications 1 and 2 below). This is a method for obtaining contrast that shows the structure of a subject by means of a phenomenon whereby an intensity pattern formed by a transmission grating that is being irradiated by X-rays on an X-ray detector varies due to slight refraction and dispersion of X-rays of a subject that is being irradiated with the same X-rays. With this method, it is possible to generally generate absorption images corresponding to conventional perspective images, refractive images showing magnitude of refraction of X-rays by the subject, and scattering images showing magnitude of scattering by the subject. In a case where grating period of a transmission grating that is used is minute, a detector is arranged at a position where the intensity pattern is strongly visible, taking into consideration fractional Talbot effect due to interference effect (so-called diffraction effect) caused by the grating. Also, in a case where the intensity pattern is so fine that it cannot be resolved directly with a detector, one more transmission grating is arranged at that position and it is possible to visualize variations in the intensity pattern by creating a moiré. It should be noted that hereafter the initial transmission grating will be called G1 and the second transmission grating will be called G2. A structure composed of G1 and G1 will be referred to as a Talbot interferometer. In operating a Talbot interferometer, it is desirable for a spatial interference distance of radiation that is irradiated on G1 to be equal to the G1 period or greater than that. This is because there is a need for radiation waves to be aligned, and with X-rays, for example, this is satisfied by using synchrotron radiation and a microfocus X-ray source. In particular, since a microfocus X-ray source is a radiation source that can be used in a laboratory it is worth noting when considering practical use. However, output of a microfocus X-ray source is generally limited, and so an exposure time of from a number of minutes to a few tens of minutes is normally required. An X-ray source that is generally used is higher power than a microfocus X-ray source, but in the first place a spatial coherence required in order to allow operation of an X-ray Talbot interferometer cannot be expected. Therefore a Talbot-Lau interferometer having a third grating (hereafter, G0) arranged in the vicinity of a general X-ray source is known. G0 behaves as a multislit. Here, a single slit of G0 will be noted. An X-ray passing through this single slit makes a downstream Talbot interferometer (G1 and G2) function. Specifically, G0 can be construed as virtually creating a microfocus X ray source. Attention will focus on X-rays that pass through the next slit in G0. Similarly, the downstream Talbot interferometer is made to operate, but with intensity pattern due to G1 at a G2 position it is possible to adjust period of G0 such that it is offset by exactly one period (strictly speaking, an integral multiple of one period). By doing this, making phase contrast shooting high speed is realized even using a conventional bright X-ray source that has low coherence while still generating moiré images using a down stream Talbot interferometer. Accordingly, it can be recognized that a Talbot-Lau interferometer is a plurality of Talbot interferometers superimposed, and also that G0 is part of a radiation source. It is also possible to arrange only G0 and G1 close to the radiation source, and omit G2, and have a method of shooting the intensity pattern that has been expanded with a direct detector, and this is called a Lau interferometer.

With either configuration, direct use of an intensity pattern or a moiré image that has been stored is scarce, and images that have been stored are processed by a given procedure using a computer, and it is possible to generate and use absorption images, refraction images, and scattering images, etc. With conventional technology it is assumed that a subject is stationary within a field of view, and a fringe scanning method is used for this purpose. A fringe scanning method is a method with which either grating is translated in its periodic direction, a plurality of intensity patterns or moiré images are photographed, and image operations are carried out. More specifically, shooting is carried out by translating either grating by 1/M of its period d, and image processing is carried out using M images that have been obtained by repeating this process M times. M is an integer of 3 or greater.

There is also a method whereby an absorption image, refraction image, and scattering image, etc., are created with a single shooting. One such method is a Fourier transform method (refer to non-patent publications 1 and 2 below). With this method, in a state where the aforementioned intensity pattern or thin stripes (carrier fringe) of a rotation moiré pattern, etc., have been created, Fourier transform is performed once on a measurement image. An absorption image is acquired by extracting only a 0 order diffraction region and applying Fourier inverse transformation; a refraction image is acquired by extracting a +1 order (or −1 order) diffraction region, having subjected that region to origin movement, then applying a Fourier inverse transformation and further calculating deflection angle of a result that has been acquired; or a scattering image is acquired by applying Fourier inverse transformation to a ratio of the 0 order and +1 order (or −1 order) diffraction regions. Since it is not necessary to perform image shooting a plurality of times, as with the fringe scanning method, there is the advantage that shooting can be made high speed. However, since spatial resolution is limited by the period of the carrier fringe, image quality is generally not good. A method of carrying out arithmetic operations for normal fringe scanning, where an intensity pattern or a moiré image pattern is matched to a pixel array of an image detector, without using Fourier transformation, has also been used. For example, if period of an intensity pattern or a moiré image pattern is made to match an M pixel portion, arithmetic computation for fringe scanning may be carried out using this M pixel value. Finally, this M pixel constitutes one pixel of an absorption image, refraction image, or scattering image that will be generated. Spatial resolution in a direction along this M pixel is lowered in accordance with period (M pixel) of the intensity pattern, similarly to with the Fourier transformation method.

Next, a case where there is a request for nondestructive analysis or diagnosis of a subject that is moved on a belt conveyor, or nondestructive testing or diagnosis to scan a wide range on the subject, will be considered. In a case of adopting a fringe scanning method where a grating is translated, in order to realize shooting of a moving subject it is necessary to complete a plurality of image measurements in fringe scanning in the time it takes for the subject to move by a distance equivalent to a target spatial resolution. Accordingly, as well as requiring high-speed shooting, the grating translation must be repeated in a short time. When creating a moving image by repeating the fringe scanning method, since the surface area of the grating is finite, it is insufficient to only translate the grating in one direction, and it is necessary to carry out reciprocal motion in order to return to the origin of the grating. This causes vibration, and it is also possible to identify a problem whereby detrimental effects impact the photographing optical system that uses an X-ray transmission grating. The technology disclosed in patent publication 5 below has therefore been proposed as technology that does not perform grating translation. With this technology M regions are formed on a pattern of the grating itself, such that phase of the grating period is shifted by a period of 1/M, in the advancement direction of the subject. Observing based on a coordinate that has been fixed on the subject, it is possible to carry out sampling of data that is required in the fringe scanning method for this coordinate as a result of moving the subject. Also, a method has been proposed of sampling of data required in a fringe scanning method by inclining a grating for generating a rotation moiré, and the subject is moved through the rotation moiré (refer to patent publication 6 below). However, in either of these cases, it is assumed that a grating pattern is perfect, and that there is no distortion.

Incidentally, as a transmission grating that is used in the technology of each of the previously described publications, generally speaking, a structure is required that has a large surface area and a high aspect ratio, and creating such a grating utilizes extremely high level technology. However, if a grating that has actually been manufactured is evaluated, it is normal for there to be slight heterogeneity in the period of the grating. If an ideally manufactured grating has been arranged precisely in a Talbot interferometer (including a case of a Talbot-Lau interferometer and a Lau interferometer), an even x-ray intensity distribution ought to be obtained on a detector surface. However, in actual fact a slight moiré pattern will be created. This causes heterogeneity of the grating period, which cannot be resolved even if the grating geometry is adjusted. As factors for creating such heterogeneity, inaccuracies at pattern drawing and transfer stages, or distortion of a grating substrate, etc., can be considered. Manufacturing a perfect grating means controlling periodic uniformity of a grating at a nm level in an area of a few square cm, and is technically an extremely difficult problem to solve.

CITATION LIST

Patent Literature

[Patent publication 1] International patent publication WO2004/058070
[Patent publication 2] U.S. Pat. No. 5,812,629
[Patent publication 3] Japanese patent laid open number 2008-145111
[Patent publication 4] Japanese patent laid-open No. 2009-240378
[Patent publication 5] International patent publication WO2015/064723
[Patent publication 6] Japanese unexamined patent publication 2013-513413

Non-Patent Literature

[Non-patent publication 1] M. Takeda, H. Ina and S. Kobayashi, "Fourier-transform method of fringe-pattern analysis for computer-based topography and interferometry," J. Opt. Soc. Am. 72, 156-160 (1982).
[Non-patent publication 2] Atsushi Momose, Wataru Yashiro, Hirohide Maikusa, Yoshihiro Takeda, "High-speed X-ray phase imaging and X-ray phase tomography with Talbot interferometer and white synchrotron radiation," Opt. Express 17, 12540-12545 (2009).

BRIEF SUMMARY AND INITIAL DESCRIPTION

The present inventors have acquired the knowledge that it is possible to compute an absorption image, a refraction image, or a scattering image, without using a normal fringe scanning method that is based on mechanical translation of a grating, by shooting a sample that moves relative to a grating, even in a case where a distorted grating is used.

The present disclosure has been implemented on the basis of the above stated knowledge. At least one object of the present disclosure is to provide technology that can bring about reduction in the cost of grating manufacture and device maintenance since a distorted grating can be used.

The present disclosure can be expressed as described in the following aspects.

(Aspect 1)

A radiographic image generating device generates an radiographic image of a sample using an intensity distribution image for radiation that has passed through the sample and a grating group that have been arranged on a path from a radiation source section to a detection section. The radiographic image generating device includes a pixel value computation section and an image computation section. The pixel value computation section determines, using a plurality of intensity distribution images for the sample that is moved in a direction that traverses the path, whether or not a point (p, q) on the sample falls in a region (Ak) on each intensity distribution image, and obtains a sum pixel value (Jk) for each region (Ak) by summing up pixel values, on each intensity distribution image, of the point (p, q) that falls in each region (Ak), and the image computation section creates a necessary radiographic image using the sum pixel values (Jk) of the regions (Ak).

(Aspect 2)

The radiographic image generating device of aspect 1, further comprising a region specifying section that is provided with an initial image computation section, an initial image determination section, and a range computation section. The initial image computation section, in a state where there is no sample, computes at least a differential phase image ($\varphi_0$) using a plurality of intensity distribution images that have been acquired while at least partially changing a positional relationship between the radiation source section, the grating group, and the detection section, the initial image determination section determines whether or not pixel values of the differential phase image are distributed continuously in a value region of $-\pi$ to $+\pi$, in the movement direction of the sample, and the range computation section determines the region (Ak) constituting a set of pixels having the pixel values of the differential phase image in a specified range.

(Aspect 3)

The radiographic image generating device of aspect 2, wherein the region specifying section further comprises a pixel number computation section, and wherein the pixel number computation section respectively computes the number of pixels that fall on a locus of the point (p, q), in each region (Ak).

(Aspect 4)

The radiographic image generating device of any one of aspects 1 to 3, used in medical applications.

(Aspect 5)

The radiographic image generating device of any one of aspects 1 to 3, used in examination applications for foodstuff, industrial parts, and industrial products.

(Aspect 6)

A radioscopic inspection apparatus comprising the radiographic image generating device of any one of aspects 1 to 3, the radiation source section, the grating group and the detection section, wherein the detection section acquires an intensity distribution image for radiation that has passed through a sample and the grating group that have been arranged on a path from the radiation source section to the detection section.

(Aspect 7)

The radioscopic inspection apparatus of aspect 6, used in medical applications.

(Aspect 8)

The radioscopic inspection apparatus of aspect 6, used in examination applications for foodstuff, industrial parts, and industrial products.

(Aspect 9)

A radiographic image generating method that generates a radiographic image for a sample, using an intensity distribution image for radiation that has passed through the sample and a grating group that have been arranged on a path from a radiation source section to a detection section. The claimed method includes a step of determining, using a plurality of intensity distribution images for the sample that is moved in a direction that traverses the path, whether or not point (p, q) on the sample falls in a region (Ak) on each intensity distribution image, and obtaining a sum pixel value (Jk) for each region (Ak) by summing up pixel values, on each intensity distribution image, of the point (p, q) that falls in each region (Ak); and a step of creating a necessary radiographic image using the sum pixel values (Jk) of the regions (Ak).

(Aspect 10)

The radiographic image generating method of aspect 9, used in medical applications.

(Aspect 11)

The radiographic image generating method of aspect 9, used in examination applications for foodstuff, industrial parts, and industrial products.

(Aspect 12)

A non-transitory computer-readable medium having a computer program stored therein, wherein execution of the computer program by a computer causes the computer to execute each of the steps described in aspect 9.

This computer program can be stored in an appropriate storage medium (for example, optical storage medium such as CD-ROM or DVD disk, magnetic storage medium such as hard disk or flexible disk, or magneto-optical storage medium such as MO disk). This computer program can be sent via communication lines such as the internet.

According to the present disclosure it is possible to provide technology that can bring about reduction in the cost of grating manufacture and device maintenance since a distorted grating can be used.

Also, according to the present disclosure, since it is not necessary to use an accurate translation mechanism for the grating, it is possible to generate a radiographic image of a subject that relatively traverses the field of view with good accuracy while keeping device cost low.

BRIEF DESCRIPTION OF THE SEVERAL VIEWS OF THE DRAWINGS

FIG. 5(*a*) to FIG. 5(*e*) show moiré fringe images that change in accordance with position of a grating in the fringe scanning method.

FIG. 9(*a*) to FIG. 9(*i*) show moving images that have been taken in accordance with movement of a sample.

DETAILED DESCRIPTION

Figure 1:
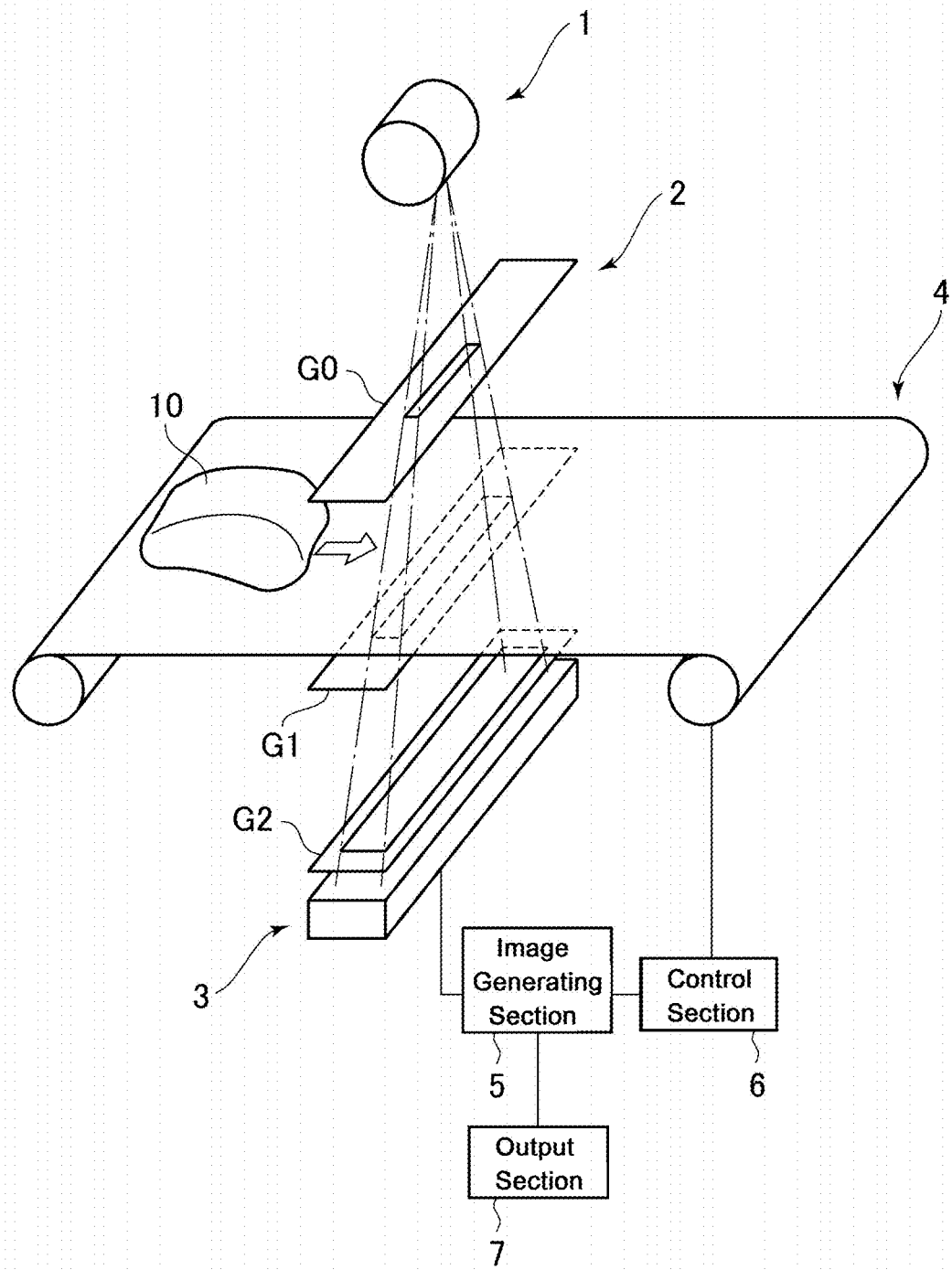
FIG. 1 is an explanatory drawing showing the schematic structure of a radioscopic inspection apparatus that uses the radiographic image generating device of one embodiment of the present disclosure.

In the following, an example of a radioscopic inspection apparatus that uses the radiographic image generating device of the present disclosure will be described.

(Radioscopic Inspection Apparatus of this Embodiment)

In the following, the structure of a radioscopic inspection apparatus of this embodiment will be described with reference to the drawings. This radioscopic inspection apparatus targets either an organism or object other than an organism as a sample 10. Also, this device can be used in medical applications or non-medical applications. As an application in non-medical fields, it is possible to exemplify the examination of foodstuffs, industrial parts, or industrial products, but these are not limiting.

(Overall Structure of Radioscopic Inspection Apparatus)

The radioscopic inspection apparatus of this embodiment (refer to FIG. 1) comprises a radiation source section 1, a grating group 2, a detection section 3, a conveyor section 4, and an image generating section 5. Further, this device is additional provided with a control section 6 and an output section 7.

(Radiation Source Section)

The radiation source section 1 is configured to radiate radiation that has transmissivity with respect to the sample 10, towards the grating group 2. Specifically, with this embodiment, an X-ray source that generates X-rays is used as the radiation source 1. As the radiation source 1, it is possible to use, for example, an X-ray source that generates X-rays (namely, radiation) as a result of irradiation of an electron beam to a target. Specific structure of the radiation source 1 can be made the same as an already known X-ray source, and so more detailed description in this regard is omitted.

(Grating Group)

The grating group 2 is provided with a plurality of gratings that are capable of transmitting radiation that has been irradiated towards this grating group 2. The grating group 2 satisfies conditions for mechanical structure and geometric configuration necessary to construct a Talbot interferometer (including the cases of a Talbot-Lau interferometer and a Lau interferometer). However, for this embodiment, conditions for constructing a Talbot interferometer are not required to satisfy conditions in the strict mathematical sense of the word, as long as they are met an extent to sufficient to make required examination possible.

Specifically, the grating group 2 of this embodiment is constituted by three gratings, namely grating G0, grating G1, and grating G2. Grating G0 is a grating for constituting a Talbot-Lau interferometer, which is one type of Talbot interferometer, and uses an absorption type grating. A micro-light source array (i.e., a Talbot interferometer if considered as a single light source), which is a structural element of a Talbot-Lau interferometer, is realized by the grating G0. As grating G1, a phase type grating is normally used, but it is also possible to use an absorption type grating. An absorption type grating is used as grating G2. It should be noted that a structure from which arrangement of G2 is omitted is also possible (Lau interferometer). Refer to patent laid open number 2012-16370.

Figure 5:
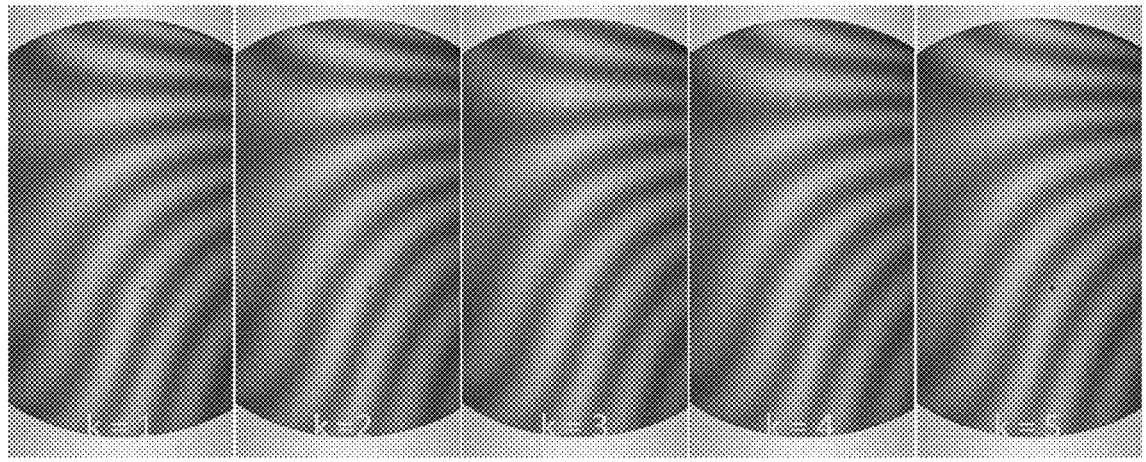
FIG. 5 is one example of a moiré fringe image attributable to grating distortion.

With the grating group 2 of this example, there is some distortion in either of the gratings. The distortion here is what is known as "offset" or "dispersion" of the grating from an ideal state, such as some kind Moiré fringe (refer to FIG. 5 which will be described later) attributable to distortion arising. This type of distortion is not specially intended and occurs naturally with normal manufacturing methods. It is obviously possible to manufacture a grating so as to intentionally impart distortion.

In points other than described above, the structures of the gratings G0-G2 can be the same as for a conventional Talbot interferometer (including the cases for a Talbot-Lau interferometer and a Lau interferometer), and so more detailed description will be omitted.

(Detection Section)

The detection section 3 of this embodiment is configured to be able to acquire an intensity distribution image of radiation that has passed through the sample 10 and the grating group 2, both of which have been arranged on a path from the radiation source section 1 to the detection section 3.

In more detail, the detection section 3 has a structure where pixels are arranged in a two dimensional array (i.e., horizontally and vertically), and is configured to detect radiation that reaches the pixels through the plurality of gratings G0-G2, for every pixel.

(Conveyor Section)

The conveyor section 4 is configured to move the sample 10 in a direction that traverses the radiation direction of the radiation (right direction within the drawing in the example of FIG. 1), with respect to the grating group 2. Specifically, the conveyor section 4 of this embodiment is constructed using a belt conveyor that moves the sample 10 in a lateral direction. Also, with this embodiment, the conveyor section 4 conveys the sample 10 so that the sample can pass through a portion of radiation passing through a space between the grating G0 and the grating G1. It should be noted that the conveyor section 4 may cause the sample 10 to pass between the grating G1 and the grating G2. It should be noted that when constructing a Lau interferometer (refer to Japanese patent laid open No. 2012-16370), the sample 10 is made to pass between the grating G1 and the detection section 3.

As a belt used in a belt conveyor, as the conveyor section 4, it is preferable to select one having high transmissivity for the radiation that is used. It should be noted that the conveyor section 4 is not limited to being a belt conveyor, and can have an appropriate structure as long as it can convey the sample 10 in a desired direction. It is also possible to have a configuration in which the sample 10 is fixed, and all of the radiation source, grating group and detection section are made to move relative to the sample 10 (including polar coordinate system movement).

(Image Generating Section)

Figure 2:
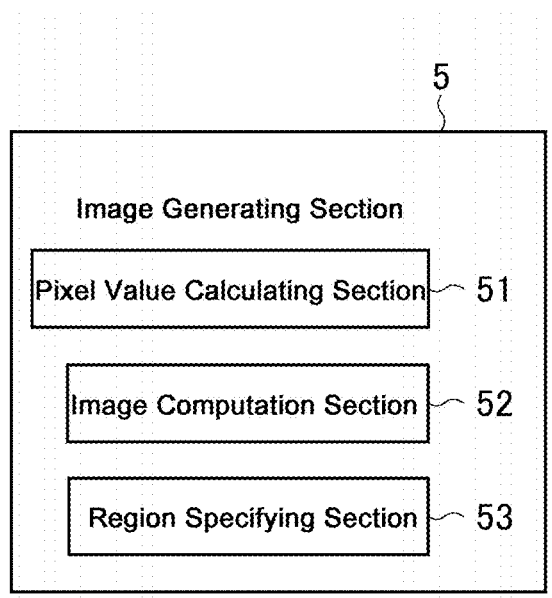
FIG. 2 is a block diagram for explaining an image generating section used in the device of FIG. 1.

The image generating section 5 (refer to FIG. 2) is provided with a pixel value computation section 51 and an image computation section 52. Further, the image generating section 5 of this embodiment is additionally provided with a region specifying section 53.

The pixel value computation section 51, using a plurality of intensity distribution images for the sample 10 that is moved in a direction that traverses an x-ray path from the radiation source section 1 to the detection section 3 (the right direction in the drawing, in the example of FIG. 1), determines whether or not a coordinate point (p, q) (described later) fixed on the sample 10 belongs in a region Ak (described later) on each intensity distribution image. Further, the pixel value computation section 51 obtains a sum pixel value Jk for point (p, q) corresponding to each region Ak, by summing pixel values on each intensity distribution image when point (p, q) is in each region Ak.

The image computation section 52 is configured to create a necessary radiographic image using the sum pixel values (Jk) corresponding to the regions (Ak).

Figure 3:
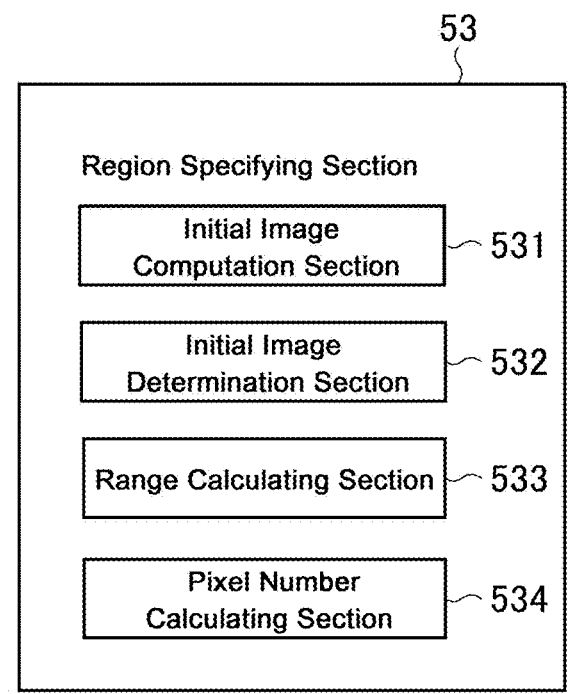
FIG. 3 is a block diagram for explaining a region specifying section used in the device of FIG. 1.

The region specifying section 53 (refer to FIG. 3) is provided with an initial image computation section 531, an initial image determination section 532, a range computation section 533, and a pixel number computation section 534.

The initial image computation section 531 is configured to compute at least a wrapped differential phase image ($\varphi_0$), using a plurality of intensity distribution images that have been acquired while at least partially changing a positional relationship between the radiation source section 1, the grating group 2 and the detection section 3 in a state where there is no sample 10. A wrapped differential phase image is an image in which a range resulting from arc tangent computation becomes from $-\pi$ to $+\pi$. Specifically, for example, a pixel value that has an original value of 1.5 $\pi$ is expressed as $-0.5\pi$.

The initial image determination section 532 is configured to determine whether or not pixel values of a wrapped differential phase image are distributed continuously in a range of from $-\pi$ to $\pi$, in the movement direction of the sample 10.

The range computation section 533 is configured to determine regions (Ak) that are sets of pixels having pixel values of a wrapped differential phase image that are within a specified range.

The pixel number computation section 534 is configured to compute a number of pixels belonging to each region (Ak).

More detailed structure of the image generating section 5 will be additionally described as description of an operation method.

(Control Section)

The control section 6 is configured to send drive signals to the conveyor section 4, and send information on the movement velocity of the sample 10 (command value or detection value) to the image generating section 5.

(Output Section)

The output section 7 is configured to be able to output images that have been generated by the image generating section 5. As the output section 7, it is possible to use a display that can present images to the user, memory means that can temporarily or permanently store images, or another appropriate device. The output section 7 may also be configured to transmit image data to another device via a network.

(Operation of the Radioscopic Inspection Apparatus of this Embodiment)

Figure 8:
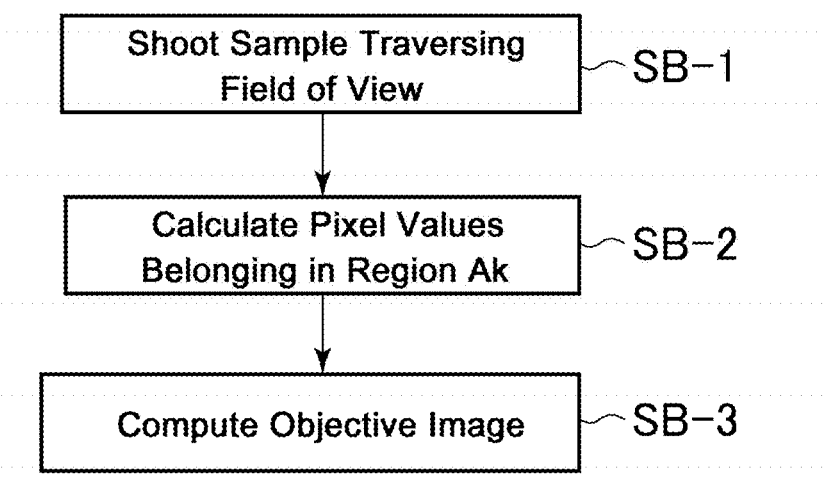
FIG. 8 is a flowchart showing an outline of an image generating method using the device of FIG. 1.

An image generating method that uses the radioscopic inspection apparatus of this embodiment will be described in the following. This method is roughly divided into region specifying stage (FIG. 4) and image generating stage (FIG. 8). Description will first be given of the region specifying stage of FIG. 4.

Figure 4:
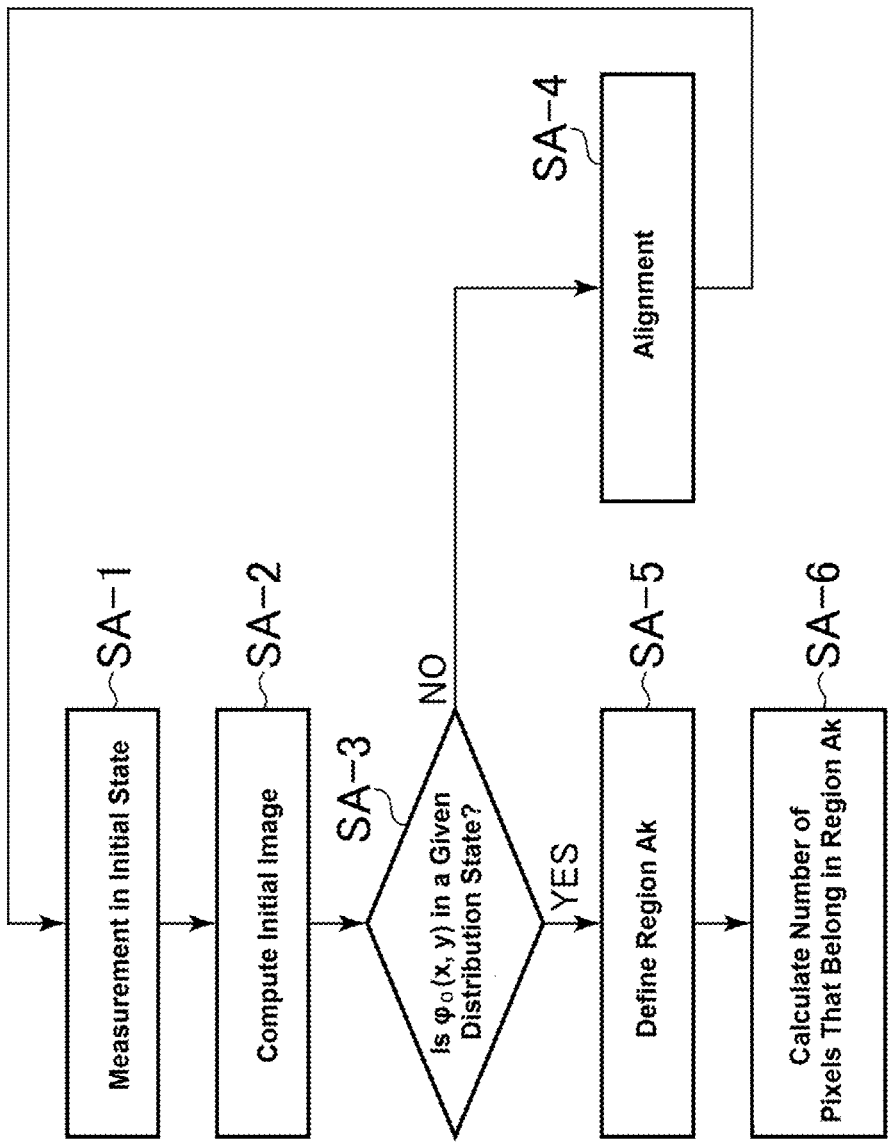
FIG. 4 is a flowchart showing an outline of an image generating method using the device of FIG. 1.

(Region Specifying Stage)
(Step SA-1 of FIG. 4)

First, the conveyor section 4 is stopped and a state where the sample 10 is not used is entered (no-sample state). In this state, a conventional fringe scanning method is carried out.

Specifically, if a grating period is made T, shooting using X-rays is carried out while moving the grating sequentially by a distance Tx1/M (M is a natural number of 3 or greater), and a plurality of intensity distribution images are acquired by the detection section 3. This image corresponds to one example of "a plurality of intensity distribution images that have been acquired while at least partially changing a positional relationship between the radiation source section 1, the grating group 2 and the detection section 3." Examples of intensity distribution images that have been acquired in this way are shown in FIG. 5(a) to FIG. 5(e). With this example, M=5. Also, with the example of FIG. 5, a moiré fringe resulting from grating distortion is generated.

(Step SA-2 of FIG. 4)

Figure 6:
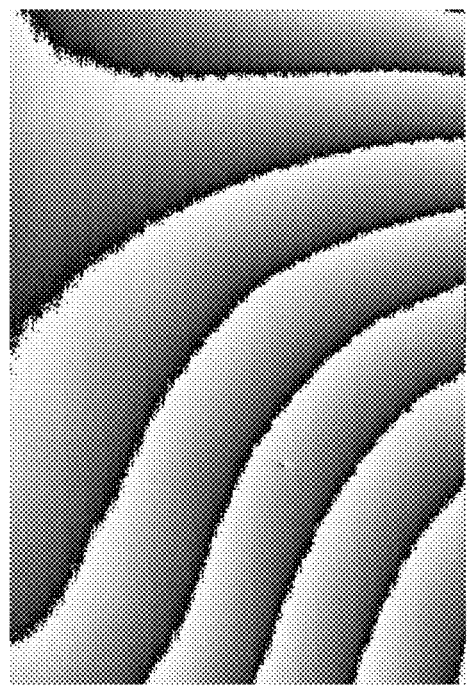
FIG. 6 is an image showing one example of a differential phase image calculated from the images of FIG. 5.

Next, the initial image computation section 531 of the region specifying section 53 computes at least a wrapped differential phase image $\varphi_0$ (x, y), as an initial image, using the plurality of intensity distribution images that have been acquired (refer to FIG. 6). Here, (x, y) represents coordinates in the field of view of the detection section 3 or in an image acquisition range. The initial image computation section 531 of this example further computes an absorption image $A_0$ (x, y) and a visibility image $V_0$ (x, y).

(Step SA-3 of FIG. 4)

Next, the initial image determination section 532 of the region specifying section 53 determines, for each y of coordinates (x, y), whether or not values of a wrapped differential phase image $\varphi_0$ (x, y) are continuously distributed in a range of ($-\pi$ to $+\pi$) in the movement direction of the sample 10 (with the example of FIG. 1, in the right direction in the drawing). Specifically, it is determined whether or not there is continuous phase change spanning $-\pi$ to $+\pi$. Since a sample 10 is not actually used at this stage, the movement direction means a direction in which the sample 10 should be moved.

If the determination in this step is No, processing advances to the step SA-4, which will be described later, while if the determination is Yes processing advances to step SA-5, which will be described later.

(Step SA-4 in FIG. 4)

In the event that, for each y of coordinates (x, y), values of a wrapped differential phase image $\varphi_0$ (x, y) are not continuously distributed in a range of $-\pi$ to $+\pi$, in the movement direction of the sample 10, grating alignment is carried out. Alignment of the grating means changing some relative arrangement conditions of the grating, including, for example, grating inclination, distance between gratings, grating curvature, etc. The alignment operation itself can be carried out manually by an operator, and can be carried out automatically using some sort of automated means. After that, previously described step SA-1 is returned to, and the subsequent steps are repeated.

(Step SA-5 in FIG. 4)

If the determination in step SA-4 was YES, then the range computation section 533 determines a range (Ak) based on values of the wrapped differential phase image $\varphi_0$ (x, y).

More specifically, if a field of view region is divided into n (where n is an integer of 3 or more), regions Ak can be defined from the following rules. It should be noted that k=1, 2, . . . , n.

$$A_k \ni (x,y), \text{ if } -\pi+2\pi(k-1)/n < \varphi_0(x,y) < -\pi+2\pi k/n$$

Figure 7:
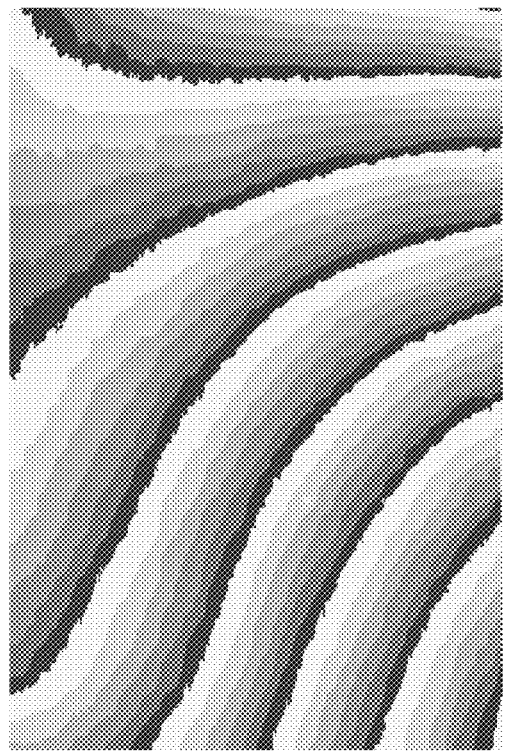
FIG. 7 is an image showing one example of region division calculated from the differential phase image of FIG. 7.

An example of regions that have been divided in this way is shown in FIG. 7. With this example, n=6. With this example, one region Ak means a portion where each of the divided regions have been interleaved. Also, the whole of the field of view region is covered by regions Ak, without overlapping.

As a result of the above processing, it is possible to specify regions Ak that the intensity distribution image should be divided into.

(Step SA-6 of FIG. 4)

Next, the pixel number computation section 534 is configured to respectively compute, for each region (Ak), a number of pixels that belong to a locus of point (p, q) of coordinates that lie on the sample 10 (that is, a locus that intersects each region accompanying movement of the sample). The locus of point (p, q) can be a locus at the time that any point on the sample intersects the field of view, and with the example of FIG. 7 it is possible to recognize a straight line from top to bottom, for example.

More specifically, the pixel number computation section 534 of this example creates, for each y, group g(y) for a number of pixels that belong in a region Ak, counted along the x axis direction, where $$g(y)=(N_1(y), N_2(y), \ldots, N_n(y)).$$

(Actual Image Generating Stage)

Next, the image generating stage shown in FIG. 8 will be described.

(Step SB-1 in FIG. 8)

First, a sample 10 that moves so as to intersect the field of view of the detection section 3 is photographed. Specifically, the detection section 3 acquires a plurality of intensity distribution images for the sample 10 that moves in a direction that intersects a path from the radiation source section 1 to the detection section 3. An example of the plurality of intensity distribution images that have been acquired in this way is shown in FIG. 9(a) to 9(i). x in the drawing shows movement direction of the sample 10. FIG. 9(a) to 9(i) shows appearance when the sample 10 is moving in the x direction within the field of view of the detection section 3.

Figure 9:
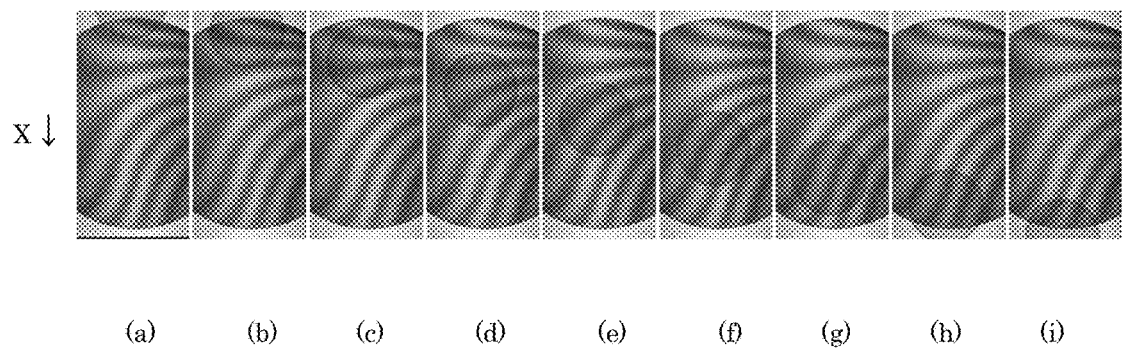
FIG. 9 is images that has been taken in accordance with movement of a sample.

It should be noted that actual photographing interval (sampling period) is shorter, and FIG. 9 shows images that have been extracted from a moiré moving image every 100 frames. Also, the intensity distribution images may be identified using I(x, y, t) in the above description. Here, x, y is a coordinate within the field of view, and t is acquisition time of the frame in question. Accordingly it is possible to express a moving image using change in t, within I(x, y, t).

This makes it possible to show fixed coordinates on the sample as shown below.

$$p=x+vt,$$

$$q=y$$

v here is speed of the sample 10 in the x axis direction.
(Step SB-2 in FIG. 8)

Next, the pixel value computation section 51 can obtain sum pixel value (Jk), for a plurality of intensity distribution images of the sample 10 that moves in a direction that traverses a path from the radiation source section 1 to the detection section 3 (refer to FIG. 9), by summing pixel values for the case where point (p, q) on the sample 10 belongs to region (Ak).

This processing can specifically be executed as follows. That is, when a point (p, q) is in a particular region AK, I(p−vt, y, t)/Nk(y) is added to stack Jk(p, q). This is carried out for all moving image frames (that is, frames corresponding to each t). Here, dividing by Nk(y) is in order to normalize (namely, average) values of pixel values I in accordance with number of pixels. Accordingly, the sum pixel value Jk in this embodiment has been normalized using number of pixels Nk.

More specifically, the procedure can be described as shown below.

when $(p,q) \in Ak, Jk(p,q) += I(p-vt,y,t)/Nk(y)$

Figure 10:
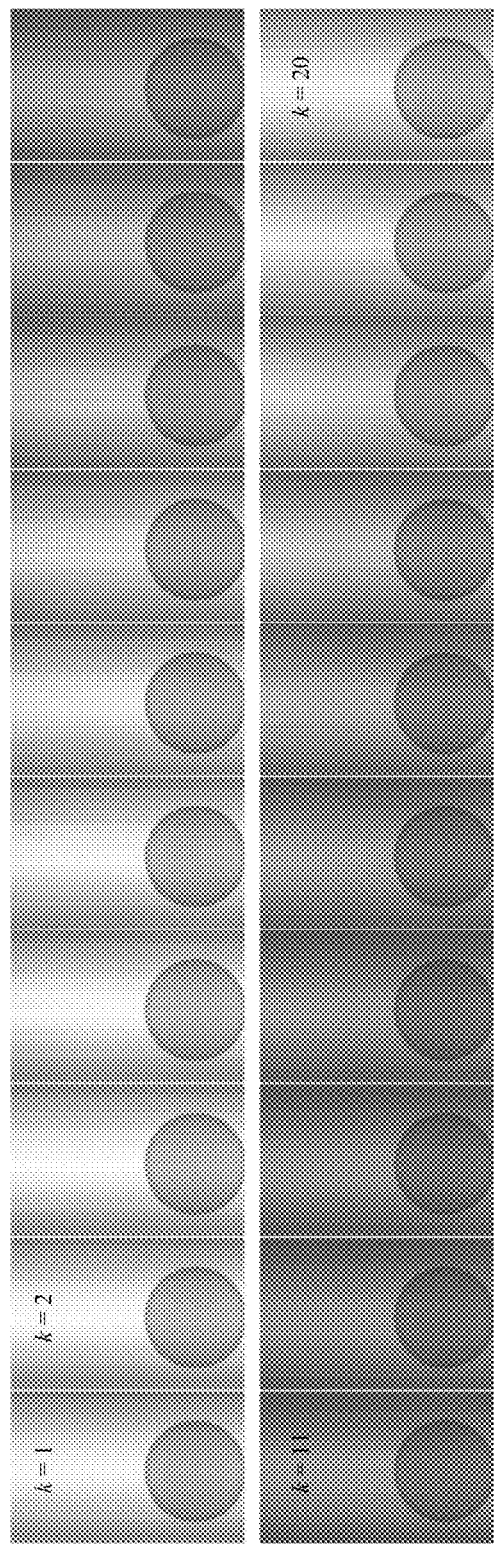
FIG. 10 shows images that have been generated using sum pixel values generated from the moving images of FIG. 9.

An example of images corresponding to this stack Jk (namely images resulting from adding all frames) is shown in FIG. 10. With this example, in $J_k(p,q)(k=1, 2, \ldots, n)$ described below, n=20.

(Step SB-3 in FIG. 8)

The image computation section 52 creates a necessary radiographic image using the sum pixel values (Jk).

More specifically, with this embodiment, using $J_k$ (p,q) (k=1, 2, . . . , n) that has been acquired, an absorption image $A_{bs}$, a refraction image $\varphi$, and a scattering image $V_{is}$ can be respectively computed as:

$$A_{bs}(p, q) = \sum_{k=1}^{n} J_k(p, q)$$

$$\varphi(p, q) = \arg\left[\sum_{k=1}^{n} J_k(p, q) \exp\left(i2\pi \frac{k}{n}\right)\right]$$

$$V_{is}(p, q) = \frac{2\left|\sum_{k=1}^{n} J_k(p, q) \exp\left(i2\pi \frac{k}{n}\right)\right|}{A_{bs}(p, q)}$$

Figure 11:
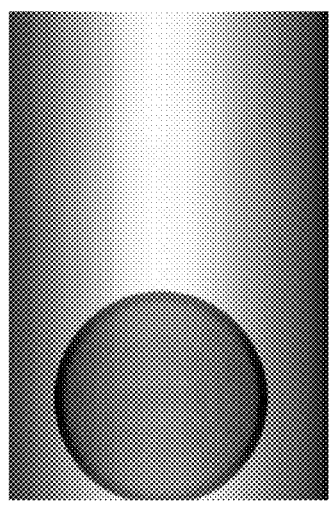
FIG. 11 shows an absorption image that has been generated from FIG. 10.
Figure 12:
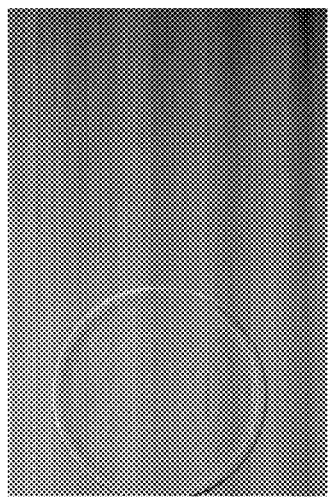
FIG. 12 shows a refractive image that has been generated from FIG. 10.
Figure 13:
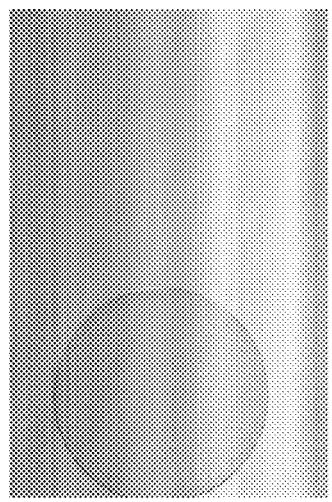
FIG. 13 shows a scattering image that has been generated from FIG. 10.

Examples of the acquired images are shown in FIG. 11 to FIG. 13. It should be noted that these are only one example of radiographic images generated as required, and it is not necessary to generate all of these. Generating other types of images is also possible.

According to this embodiment, at the image creation stage it is possible to create a required radiographic image without using a fringe scanning method (method of moving a grating intermittently) as with the prior art. As a result, with this embodiment it is possible to generate a radiographic image at high speed, even in a case where the sample and the device move relatively (normally the sample side moves), and it is possible to make relative movement velocity between the sample and the device faster.

Also, according to this embodiment, since it is possible to generate a radiographic image of good precision even if a grating shape and arrangement conditions are not perfect, it is possible to keep device manufacturing cost and maintenance costs low.

Modified Example

An image generating device of a modified example will be described in the following.

With the previously described embodiment, when a point (p, q) is in a particular region Ak, Jk is generated by adding I(p−vt, y, t)/Nk(y) to stack Jk(p, q). Here, if it can not be assumed that X-ray intensity and image sharpness are even, an error can arise within an image.

With this modified example, therefore, in computation of $J_k$ a coefficient for reducing the effect of this error is introduced. Specifically, for coordinate (p, q) fixed on the sample (here, p=x+vt, q=y), by computing when $(p,q) \in Ak, Jk(p,q) += I(p-vt,y,t)/Nk(y)/A_0(p-vt,y)$ for all I(x,y,t) it is possible to acquire Jk. That is, with this modified example intensity correction is intended as a result of dividing I by coefficient $A_0$ (p–vt,y). It should be noted that this coefficient $A_0$ is the same as the previously described absorption image data, and so the same reference numeral is used.

Other structure and operation of the modified example are the same as the previously described embodiment, and so more detailed description is omitted.

Practical Example

A practical example that uses the procedure of the previously described embodiment will be described based on FIG. 14 to FIG. 16.

Figure 14:
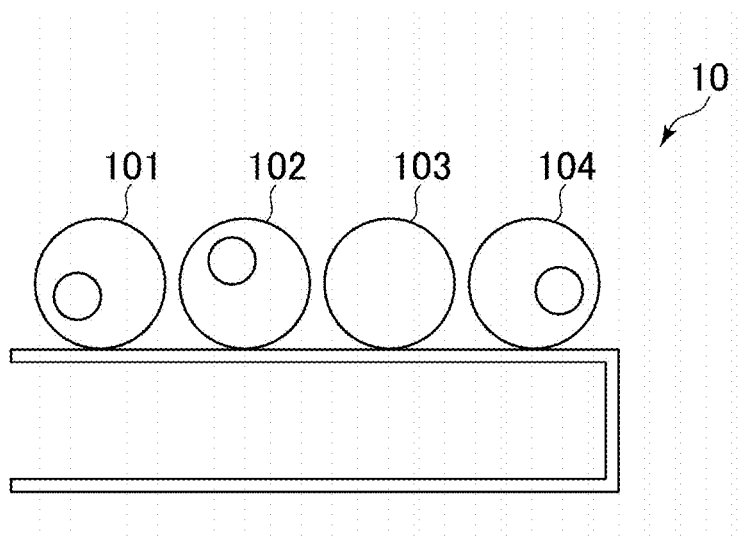
FIG. 14 is an explanatory drawing for describing a sample used in specific practical examples.

With this practical example, the sample 10 shown in FIG. 14 is used. This sample 10 has a polyethylene sphere 101 containing an air portion inside (shown by the small circle in the drawing), a polypropylene sphere 102 containing an air portion inside, a PMMA sphere 103, and a POM sphere 104 containing an air portion inside. These spheres 101 to 104 all have the same diameter (7.9 mm), and are arranged in a one-dimensional direction (the lateral direction in FIG. 14).

Figure 15A:
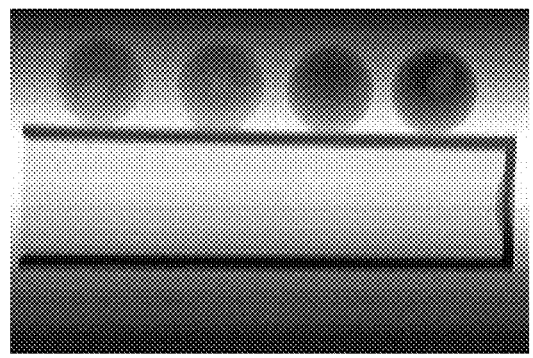
FIG. 15 shows radiographic images that have been acquired in a modified example, with FIG. 15a showing an absorption image, FIG. 15b showing a refractive image, and FIG. 15c showing a scattering image.
Figure 15B:
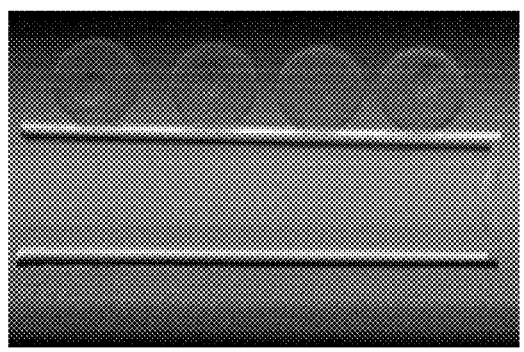
Figure 15C:
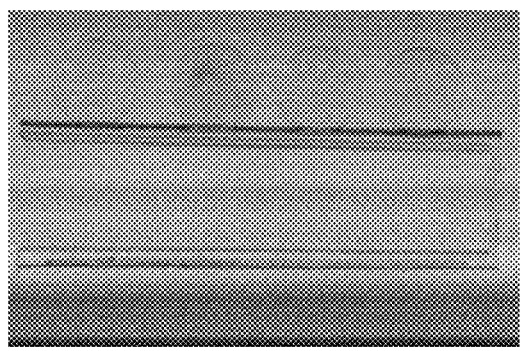

First, radiographic images that have been acquired with the method of this embodiment are shown in FIG. 15A to FIG. 15c. As will be understood from these images, while it is possible to acquire a radiographic image with high precision, unnecessary contrast is observed. It should be noted that the scanning direction of the sample in this practical example is the horizontal direction in the drawing.

Figure 16A:
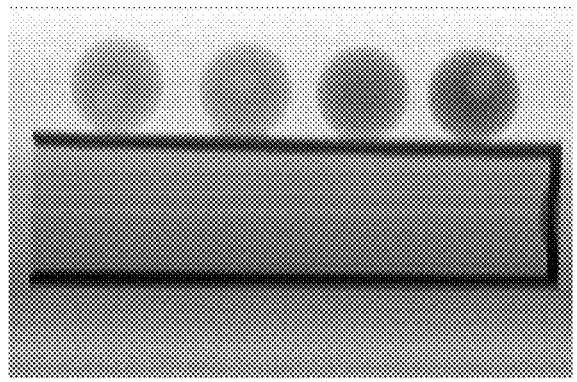
FIG. 16 shows radiographic images that have been acquired in a modified example, after correction, with FIG. 16a showing an absorption image, FIG. 16b showing a refractive image, and FIG. 16c showing a scattering image.
Figure 16B:
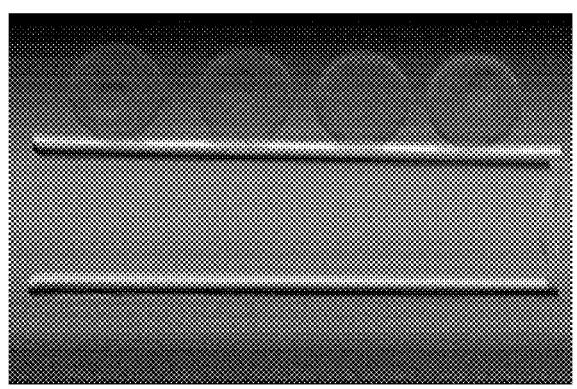
Figure 16C:
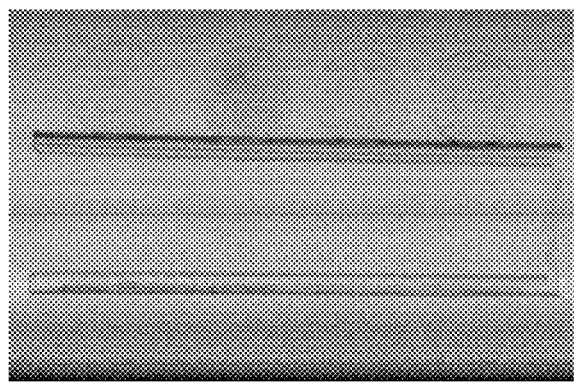

Next, radiographic images that have been acquired with the method of the modified example are shown in FIG. 16a to FIG. 16c. As will be understood from these images it is possible to acquire radiographic images in which errors have been reduced.

It should be noted that descriptions for each of the embodiments and the practical example are merely simple examples, and do not show the essential structure of the present disclosure. The structure of each part is not limited to the above description as long as it falls within the scope of the present disclosure.

For example, with the previously described embodiment an x-ray source has been used as the radiation source section, but it is also possible to use another radiation source that has transmissivity with respect to the sample, for example, a neutron source. Obviously, in this case, the detection section is capable of detecting the radiation source that is used.

DESCRIPTION OF THE NUMERALS $A_k$ region
$G_0$ to $G_2$ grating
$J_k$ sum pixel value
$N_k$ number of pixels
1 radiation source section
2 grating group
3 detection section
4 conveyer section
5 image creation section
51 pixel value computation section
52 image computation section
53 region specifying section
531 initial image computation section
532 initial image determination section
533 range computation section
534 pixel number computation section
6 control section
7 output section
10 sample The various embodiments and aspects described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A radiographic image generating device, for generating an radiographic image for a sample, using an intensity distribution image for radiation that has passed through the sample and a grating group that have been arranged on a path from a source section to a detection section, comprising:
a pixel value computation section; and
an image computation section,
wherein the pixel value computation section determines, using a plurality of intensity distribution images for the sample that is moved in a direction that traverses the path, whether or not point (p, q) on the sample falls in a region (Ak) on each intensity distribution image, and obtains a sum pixel value (Jk) for each region (Ak) by summing up pixel values, on each intensity distribution image, of the point (p, q) that falls in each region (Ak), and
wherein the image computation section creates a necessary radiographic image using the sum pixel values (Jk) of the regions (Ak).

2. The radiographic image generating device of claim 1, further comprising a region specifying section, wherein;
the region specifying section comprises an initial image computation section, an initial image determination section, and a range computation section,
the initial image computation section, in a state where there is no sample, computes at least a differential phase image ($\varphi_0$) using a plurality of intensity distribution images that have been acquired while at least partially changing a positional relationship between the radiation source section, the grating group, and the detection section,
the initial image determination section determines whether or not pixel values of the differential phase image are distributed continuously in a value region of $-\pi$ to $+\pi$, in the movement direction of the sample, and
the range computation section determines the region (Ak) such that the pixel values of the differential phase image constitute a set of pixels in a specified range.

3. The radiographic image generating device of claim 2, wherein the region specifying section further comprises a pixel number computation section, and
wherein the pixel number computation section respectively computes a number of pixels that fall on a locus of the point (p, q), in each region (Ak).

4. The radiographic image generating device of claim 1, used in medical applications.

5. The radiographic image generating device of claim 1, used in examination applications for foodstuff, industrial parts and industrial products.

6. A radioscopic inspection apparatus comprising the radiographic image generating device of claim 1, including the radiation source section, the grating group, and a detection section, wherein the detection section acquires an intensity distribution image for radiation that has passed through a sample and the grating group that have been arranged on a path from the radiation source section to the detection section.

7. The radioscopic inspection apparatus of claim 6, used in medical applications.

8. The radioscopic inspection apparatus of claim 6, used in examination applications for foodstuff, industrial parts and industrial products.

9. A radiographic image generating method, for generating a radiographic image for a sample, using an intensity distribution image for radiation that has passed through the sample and a grating group that have been arranged on a path from a radiation source section to a detection section, comprising:

determining, using a plurality of intensity distribution images for the sample that is moved in a direction that traverses the path, whether or not point (p, q) on the sample falls in a region (Ak) on each intensity distribution image, obtaining a sum pixel value (Jk) for each region (Ak) by summing up pixel values, on each intensity distribution image, of the point (p, q) that falls in each region (Ak), and creating a necessary radiographic image using the sum pixel values (Jk) of the regions (Ak).

10. The radiographic image generating method of claim 9, used in medical applications.

11. The radiographic image generating method of claim 9, used in examination applications for foodstuff, industrial parts and industrial products.

12. A non-transitory computer-readable medium having a computer program stored thereon, wherein execution of the computer program by a computer causes the computer to:

determine, using a plurality of intensity distribution images for the sample that is moved in a direction that traverses the path, whether or not point (p, q) on the sample falls in a region (Ak) on each intensity distribution image, obtain a sum pixel value (Jk) for each region (Ak) by summing up pixel values, on each intensity distribution image, of the point (p, q) that falls in each region (Ak), and create a necessary radiographic image using the sum pixel values (Jk) of the regions (Ak).

\* \* \* \* \*